United States Patent [19]

Zannucci et al.

[11] 4,202,788

[45] May 13, 1980

[54] STABILIZATION OF AQUEOUS P-BENZOQUINONES

[75] Inventors: Joseph S. Zannucci; John W. Thompson, both of Kingsport, Tenn.

[73] Assignee: Eastman Kodak Company, Rochester, N.Y.

[21] Appl. No.: 11,603

[22] Filed: Feb. 12, 1979

[51] Int. Cl.$^2$ ............................................. C09K 3/00
[52] U.S. Cl. ................................. 252/182; 252/397;
252/400 R; 252/404; 260/45.7 R; 260/45.75 N;
430/499; 430/566; 430/607
[58] Field of Search ........ 260/396 R, 45.7 R, 45.75 N;
252/400 R, 182, 397, 404; 96/66 R, 66.3, 66.4,
66.5, 109; 8/1 R

[56] References Cited

U.S. PATENT DOCUMENTS

| | | | |
|---|---|---|---|
| 3,065,074 | 11/1968 | Rogers | 96/29 D |
| 3,396,022 | 8/1968 | Dersch | 96/109 |
| 3,519,428 | 7/1970 | Ishikawa et al. | 96/95 |
| 3,965,050 | 6/1976 | Shimogaua et al. | 260/457 R |
| 4,010,036 | 3/1977 | Suga et al. | 96/109 |
| 4,042,764 | 8/1977 | Gratani et al. | 260/45.7 R |
| 4,097,454 | 6/1978 | Tozzi et al. | 252/404 |

*Primary Examiner*—Richard E. Schafer
*Assistant Examiner*—J. Lloyd Barr

*Attorney, Agent, or Firm*—Donald W. Spurrell; Daniel B. Reece, III

[57] ABSTRACT

The storage stability of aqueous p-benzoquinone and in general compounds of the formula

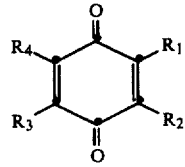

where $R_1$, $R_2$, $R_3$, and $R_4$ may be the same or different and are selected, for example, from hydrogen, hydroxyl, cyano, halogen, carboxylic acid or ester, thio, thioethers, sulfonic acid or ester groups, sulfinic acid or ester groups, amino, alkylamino, dialkylamino, arylamino, diarylamino, alkylarylamino, cycloalkylamino, acylamino, acyloxy, acyl, nitro, $C_1$–$C_{20}$ substituted or unsubstituted, saturated or unsaturated, straight chain, branched or cyclic aliphatic moieties, $C_6$–$C_{32}$ substituted or unsubstituted aromatic moieties, and $C_1$–$C_{18}$ alkoxy moieties, are improved by the addition of water-soluble, acidic or neutral inorganic salts of Periodic Table Group IA elements, Group IIA elements, and nickel. Such salts are typified by $CaCl_2$, $KCl$, $MgSO_4$, $NaBr$, $NaCl$, and $NiCl_2$.

12 Claims, No Drawings

STABILIZATION OF AQUEOUS P-BENZOQUINONES

This invention concerns the stabilization of aqueous suspensions or wet cake of p-benzoquinone type compounds. p-Benzoquinone (PBQ) and its derivatives are used in photography, as reagents, as stabilizers for vinyl compounds, and in the manufacturing of dyes. PBQ is usually sold as a dry crystalline powder. Since the drying process is an energy intensive, expensive process, there is an economic advantage to using PBQ as an aqueous suspension, for example, from about 98% down to about 15% by weight p-benzoquinone or less in water, or a wet presscake. Before being dried, the PBQ presscake typically contains about 8–15% by weight of water. The wet cake or dilute aqueous suspension is suitable for use in many applications, however, its market is severely limited because of poor storage stability. While dry PBQ can be stored for many months without a noticeable change in color or performance, wet PBQ can only be stored for a few weeks before turning black and losing its stabilization effectiveness.

In accordance with the present invention we have discovered that water-soluble, acidic or neutral salts of Periodic Table Group IA elements, Group IIA elements, and nickel are effective stabilizers for wet PBQ. For example, unstabilized PBQ presscake turns black on aging for 200 hours at 50° C. while PBQ presscake containing neutral salts of Group IA elements such as NaCl, NaBr, and $Na_2SO_4$, and acidic salts of Group IIA such as $CaCl_2$ and $MgSO_4$ remain yellow. Water-insoluble salts of Group IIA elements such as $CaCO_3$, $CaSO_4$, and $Ca_3(PO_4)_2$ are not effective stabilizers, while water-soluble basic salts of Group IA elements $Na_3PO_4$, $NaC_2H_3O_2$, $Na_2SiO_3$, and $Na_2B_4O_7$ and ammonium salts such as $NH_4Cl$ and $(NH_4)_2SO_4$ accelerate the degradation of the wet PBQ. Transition metal salts such as $FeCl_2$, $FeCl_3$, $MnCl_2$, CuCl, and $CuCl_2$, with the exception of nickel, either have no significant effect on the stability of the PBQ or accelerate its degradation. Salts of Group IIB elements such as $ZnCl_2$, Group IIIA elements such as $AlCl_3$, and Group IVA elements such as $SnCl_2$ also are not effective stabilizers.

The present invention is defined as a stable composition of matter comprising in an aqueous system a compound of the formula

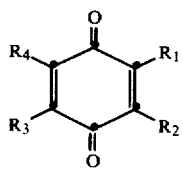

where $R_1$, $R_2$, $R_3$, and $R_4$ may be the same or different and are selected from hydrogen; hydroxyl; cyano; nitro; halogen; straight or branched alkyl and alkylene of 1–20 carbons both of which may be substituted with 1–3 groups selected from formyl, formyloxy, alkoxycarbonyl of 1–8 carbons, alkoxycarbonyloxy of 1–8 carbons, carbamoyl, alkylcarbamoyl of 1–8 carbons, —CN, alkoxy of 1–8 carbons, and aryl and cycloalkyl of 6–10 carbons each of which also may be substituted with 1–3 halogens, alkyl of 1–8 carbons, alkoxy of 1–8 carbons, and —CN; mercapto; thioethers of 1–10 carbons; alkylthio of 1–10 carbons; sulfonic or sulfinic acid or ester groups of 1–10 carbons; amino; alkylamino of 1–8 carbons; dialkylamino of 2–16 carbons; alkylarylamino of 1–8 carbons in the alkyl group and 6–10 carbons in the aryl group; arylamino of 6–10 carbons which may be substituted with 1–3 halogens, —NO₂, alkyl of 1–8 carbons, alkoxy of 1–8 carbons, and —CN; alkoxycarbonyl of 1–8 carbons; alkoxycarbonyloxy of 1–8 carbons; carbamoyl; alkylcarbamoyl of 1–8 carbons; diarylamino of 12 to 20 carbons which may be substituted with 1–3 halogens, alkyl of 1–8 carbons, alkoxy of 1–8 carbons, and —CN; cycloalkylamino which may be substituted with 1–3 halogens, alkyl of 1–8 carbons, alkoxy of 1–8 carbons, and —CN; acyl, acylamino and acyloxy of straight or branched alkyl of 1–20 carbons or aryl of 6–10 carbons, each of which may be substituted with halogen, alkyl or alkoxy of 1–8 carbons, nitro, or cycloalkyl of 5–18 carbons which may be substituted with 1–3 halogens, alkyl of 1–8 carbons, alkoxy of 1–8 carbons, or —CN; aryl of 6–32 carbons which may be substituted with 1–3 halogens, alkyl of 1–8 carbons, alkoxy of 1–8 carbons, or —CN; and alkoxy of 1–20 carbons which may be substituted with 1–3 halogens, alkoxy of 1–8 carbons, and —CN; admixed with from about 0.5 to about 25.0% by weight of one or more water-soluble acidic or neutral inorganic salts of Groups IA and IIA of the Periodic Table, or of nickel. The preferred salts are $CaCl_2$, $Na_2SO_4$, KCl, $MgSO_4$, NaBr, NaCl, and $NiCl_2$, each of which may be used alone or with others in a total concentration preferably of from about 1.0% to about 15% by weight of the p-benzoquinone compound. The most preferred salts are NaCl, $CaCl_2$, $Na_2SO_4$, and NaBr.

The following examples and tables will further illustrate the invention.

EXAMPLE 1

Into a 6-in. × 13-in. × 1.5-mil thick polyethylene bag were placed 22.5 g of wet p-benzoquinone (11.1% water) and 2.5 g of stabilizer. The contents of the bag were kneaded until it was judged that the sample was homogeneous and then the top of the bag was rolled down to the sample. The bagged sample was then placed into a two-ounce glass bottle, the bottle loosely capped, and then placed in a 50° C. oven. After 200 hours, the bottle was removed and the color noted. The results are shown in Table I.

EXAMPLE 2

Water (105 g), dry p-benzoquinone (45 g), and various amounts of stabilizer were stirred for 5 minutes in a 200 ml beaker. The mixture was then filtered through 9 cm filter paper (Sargent-Welch, grade S-32915-D) using house vacuum. The precipitate was allowed to remain on the filtering apparatus under house vacuum for an additional five minutes. Using this procedure, a wet p-benzoquinone cake containing approximately 10% water is obtained. The precipitate was placed in 6-in. × 13-in. × 1.5-mil thick plastic bags and tested for color stability. The results are shown in Table II.

TABLE I

| Effect of Selected Inorganic Salts on the Oven Stability of p-Benzoquinone Presscake[1] | |
|---|---|
| Inorganic Salt[2] | Color After 200 Hours Aging at 50° C. |
| None | Black |
| $AlCl_3$[3] | Black |
| $CaCl_2$ | Yellow |
| $Ca_3(PO_4)_2$ | Black |

TABLE I-continued
Effect of Selected Inorganic Salts on the Oven Stability of p-Benzoquinone Presscake[1]

| Inorganic Salt[2] | Color After 200 Hours Aging at 50° C. |
|---|---|
| CaSO$_4$[3] | Olive |
| CaCO$_3$ | Black |
| CuCl | Black |
| CuCl$_2$ | Black |
| FeCl$_2$[3] | Black |
| FeCl$_3$[3] | Black |
| KCl | Dark Yellow |
| MgSO$_4$ | Yellow |
| MnCl$_2$ | Black |
| NaBr | Yellow |
| Na$_2$SO$_4$ | Yellow |
| NaCl | Yellow |
| Na$_3$PO$_4$[3] | Black |
| Na$_2$HPO$_4$ | Black |
| NaC$_2$H$_3$O$_2$ | Black |
| Na$_2$B$_4$O$_7$[3] | Black |
| Na$_2$SiO$_3$ | Black |
| NaBr | Yellow |
| NaNO$_3$ | Dark Yellow |
| NH$_4$Cl | Black |
| (NH$_4$)$_2$SO$_4$ | Black |
| NiCl$_2$[3] | Dark Yellow |
| SnCl$_2$[3] | Black |
| ZnCl$_2$ | Black |

[1] Wet PBQ presscake contains 11.1% water.
[2] The inorganic salt concentration is 10% based on weight of presscake.
[3] Hydrated salt.

TABLE 2
Effect of Stabilizer Concentration on the Oven Stability of Wet p-Benzoquinone[1]

| Inorganic Salt | Concentration (%)[2] | Color After 200 Hours Aging at 50° C. |
|---|---|---|
| None | — | Black |
| NaCl | 1.25 | Olive |
| NaCl | 2.5 | Yellow |
| NaCl | 5.0 | Yellow |
| NaCl | 10.0 | Yellow |
| CaCl$_2$ | 1.25 | Olive |
| CaCl$_2$ | 2.5 | Yellow |
| CaCl$_2$ | 5.0 | Yellow |
| CaCl$_2$ | 10.0 | Yellow |

[1] Wet presscake contains about 10% water.
[2] Based on weight of presscake.

The following table lists some specific benzoquinones of the present invention.

TABLE 3

| R$_1$ | R$_2$ | R$_3$ | R$_4$ |
|---|---|---|---|
| —Cl | —H | —H | —H |
| —C$_6$H$_4$ | —H | —H | —H |
| —CH$_3$ | —H | —H | —H |
| —Cl | —H | —Cl | —H |
| —CH$_3$ | —H | —CH$_3$ | —H |
| —CH$_3$ | —CH$_3$ | —CH$_3$ | —H |
| —H | —H | —H | —H |
| —NO$_2$ | —NO$_2$ | —OH | —H |
| —Cl | —Cl | —Cl | —Cl |
| —OCH$_3$ | —H | —H | —H |
| —OCH$_3$ | —CH$_3$ | —H | —H |
| —C$_2$H$_5$ | —H | —H | —H |
| —CH$_3$ | —H | —CH(CH$_3$)$_2$ | —H |
| —C$_3$H$_5$ | —H | —H | —H |
| —CN | —H | —H | —H |
| —CH$_2$CHC(CH$_3$)$_2$ | —H | —H | —H |
| —CH$_2$OH | —H | —H | —H |
| —CH$_3$ | —CH$_2$OH | —OH | —CH$_3$ |
| —(CH$_2$)$_2$CH=CHCO$_2$H | —H | —H | —OCH$_3$ |
| —CH$_3$ | —CH$_2$OH | —CH$_3$ | —OH |
| —CH$_3$ | —OH | —CH$_2$CH(CH$_3$)$_2$ | —OH |
| —CH$_3$ | —OH | —CH$_2$CH(CH$_3$)$_2$ | —H |
| —CH$_3$ | —CH$_3$ | —OCH$_3$ | —OCH$_3$ |
| —C$_2$H$_5$ | —OH | —H | —OH |
| —CH$_3$ | —NHCH$_3$ | —OCH$_3$ | —NHCH$_3$ |
| —H | —C$_2$H$_4$—C$_6$H$_5$ | —H | —OCH$_3$ |
| —O—C$_6$H$_5$ | —H | —H | —OCH$_3$ |
| —C$_{15}$H$_{29}$-n | —OH | —H | —OCH$_3$ |
| —C$_{21}$H$_{43}$-n | —OH | —CH$_3$ | —OH |
| —H | —OCH$_3$ | —CH$_3$ |  |
| —C$_6$H$_5$ | —OH | —C$_6$H$_5$ | —OH |
| —C$_6$H$_5$-p-C$_4$H$_9$ | —OH | 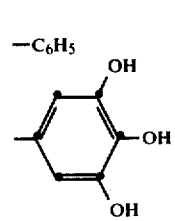 | —OH |

TABLE 3-continued

| R₁ | R₂ | R₃ | R₄ |
|---|---|---|---|
| —OH | —COCH₂CH₂Ph | —OCH₃ | —OH |
| —C₆H₅-m-OH | —H | —H | —C₆H₅-m-OH |
| —C₆H₅ | —OH | —C₆H₅ | —CH₃ |
| —C₆H₅-p-OH | —OH | —C₆H₅-p-OH | —OH |
| —C₆H₅-p-OH | —OCOPh | —C₆H₅-p-OH | —OCOPh |
| —C₆H₅-p-OCH₂OCH₃ | —Cl | —C₆H₅-p-OCH₂OCH₃ | —Cl |
| —C₆H₅-m,p-OCH₃ | —Cl | —C₆H₅-p-OCH₃ | —Cl |
| —OH | —COCH=CHPh | —OCH₃ | —OCH₃ |
| —C₆H₅-o-CO₂H | —CH=CH—CH=CHCO₂H | —C₆H₅-o-CO₂H | —OH |
| —OH | —OH | —OH | —OH |

The invention has been described in detail with particular reference to preferred embodiments thereof, but it will be understood that variations and modifications can be effected within the spirit and scope of the invention.

We claim:

1. A stable composition of matter comprising in an aqueous system a compound of the formula

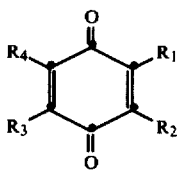

where $R_1$, $R_2$, $R_3$ and $R_4$ may be the same or different and are selected from hydrogen; hydroxyl; cyano; nitro; halogen; straight or branched alkyl and alkylene of 1–20 carbons both of which may be substituted with 1–3 groups selected from formyl, formyloxy, alkoxycarbonyl of 1–8 carbons, alkoxycarbonyloxy of 1–8 carbons, carbamoyl, alkylcarbamoyl of 1–8 carbons, —CN, alkoxy of 1–8 carbons, and aryl and cycloalkyl of 6–10 carbons each of which also may be substituted with 1–3 halogens, alkyl of 1–8 carbons, alkoxy of 1–8 carbons, and —CN; mercapto; thioethers of 1–10 carbons; alkylthio of 1–10 carbons; sulfonic or sulfinic acid or ester groups of 1–10 carbons; amino; alkylamino of 1–8 carbons; dialkylamino of 2–16 carbons; alkyl arylamino of 1–8 carbons in the alkyl group and 6–10 carbons in the aryl group; arylamino of 6–10 carbons which may be substituted with 1–3 halogens, —NO₂, alkyl of 1–8 carbons, alkoxy of 1–8 carbons, and —CN; alkoxycarbonyl of 1–8 carbons; alkoxycarbonyloxy of 1–8 carbons; carbamoyl; alkylcarbamoyl of 1–8 carbons; diarylamino of 12 to 20 carbons which may be substituted with 1–3 halogens, alkyl of 1–8 carbons, alkoxy of 1–8 carbons, and —CN; cycloalkylamino which may be substituted with 1–3 halogens, alkyl of 1–8 carbons, alkoxy of 1–8 carbons, and —CN; acyl, acylamino and acyloxy of straight or branched alkyl of 1–20 carbons or aryl of 6–10 carbons, each of which may be substituted with halogen, alkyl or alkoxy of 1–8 carbons, nitro, or cycloalkyl of 5–18 carbons which may be substituted with 1–3 halogens, alkyl of 1–8 carbons, alkoxy of 1–8 carbons, or —CN; aryl of 6–32 carbons which may be substituted with 1–3 halogens, alkyl of 1–8 carbons, alkoxy of 1–8 carbons, or —CN; and alkoxy of 1–20 carbons which may be substituted with 1–3 halogens, alkoxy of 1–8 carbons, and —CN; admixed with from about 0.5 to about 25.0% by weight of one or more water-soluble acidic or neutral inorganic salts of Groups IA and IIA elements of the Periodic Table, or of nickel.

2. The composition of claim 1 wherein the salts are selected from CaCl₂, KCl, MgSO₄, NaBr, NaCl, Na₂SO₄, NaNO₃, and NiCl₂, each of which may be used alone or with others in a total concentration preferably of from about 1.0% to about 15% by weight of the p-benzoquinone compound.

3. The composition of claim 1 wherein the salt is NaCl.

4. The composition of claim 1 wherein the salt is CaCl₂.

5. The composition of claim 1 wherein the salt is Na₂SO₄.

6. The composition of claim 1 wherein the salt is NaBr.

7. The composition of claim 1 wherein the salt is MgSO₄.

8. The composition of claim 1 wherein the salt is KCl.

9. The composition of claim 1 wherein $R_1$ through $R_4$ are selected from —H, —Cl, —C₆H₅ and —CH₃.

10. The composition of claim 1 wherein the compound is p-benzoquinone and the salts are selected from NaCl, CaCl₂ and Na₂SO₄.

11. The composition of claim 1 wherein the compound is p-benzoquinone in water at a concentration of from about 15% to about 98% by weight.

12. The composition of claim 1 wherein the compound is p-benzoquinone in water at a concentration of from about 92% to about 85% by weight.

* * * * *